(12) United States Patent
Gurny et al.

(10) Patent No.: US 6,440,460 B1
(45) Date of Patent: Aug. 27, 2002

(54) PHARMACEUTICAL COMPOSITIONS CONTAINING BUFFERED ORTHO ESTER POLYMERS

(75) Inventors: Robert Gurny; Monia Zignani, both of Genève; Cyrus Tabatabay, Bernex, all of (CH)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/117,359

(22) PCT Filed: Feb. 26, 1997

(86) PCT No.: PCT/EP97/00906

§ 371 (c)(1),
(2), (4) Date: Jul. 27, 1998

(87) PCT Pub. No.: WO97/32606

PCT Pub. Date: Sep. 12, 1997

(30) Foreign Application Priority Data

Mar. 5, 1996 (EP) .............................. 96103391

(51) Int. Cl.[7] .......................... A61K 9/10; A61K 47/34
(52) U.S. Cl. ........................................ 424/486; 424/426
(58) Field of Search ................... 424/486, 426, 424/428; 514/772.3

(56) References Cited

U.S. PATENT DOCUMENTS

| 4,093,709 A |   | 6/1978 | Choi et al. |
| 4,138,344 A | * | 2/1979 | Choi et al. |
| 4,268,643 A | * | 5/1981 | Radici et al. |
| 4,346,709 A | * | 8/1982 | Schmitt |
| 5,030,457 A |   | 7/1991 | Ng et al. |
| 5,700,485 A | * | 12/1997 | Berde et al. |

FOREIGN PATENT DOCUMENTS

| WO | WO 91/03510 | 3/1991 |
| WO | WO 93/00383 | 1/1993 |

\* cited by examiner

*Primary Examiner*—Edward J. Webman
(74) *Attorney, Agent, or Firm*—Carlos A. Fisher; Martin A. Voet; Robert J. Baran

(57) ABSTRACT

A pharmaceutical composition for the controlled release of therapeutic agents from carboxylic acid ortho ester polymers contains a pharmaceutically acceptable salt of an acid, which together with the acid R1-COOH liberated from the decomposition of the ortho ester polymer forms a buffer system in a physiologically acceptable pH range.

8 Claims, 1 Drawing Sheet

-○- POE 063 (Mw 6'800) + 1% 5-FU
-●- POE 063 (Mw 6'800) + 1% 5-FU+ 0.5% sodium acetate \* Dissolution of POE

- ○ - POE 063 (Mw 6'800) + 1% 5-FU
- ● - POE 063 (Mw 6'800) + 1% 5-FU + 0.5% sodium acetate

* Dissolution of POE

- ○ - POE (Mw 6'800) + 5-FU 1%
- ● - POE (Mw 6'800) + 5-FU 1% + sodium acetate 0.5 %

PHARMACEUTICAL COMPOSITIONS CONTAINING BUFFERED ORTHO ESTER POLYMERS

The present invention relates to a pharmaceutical composition for the controlled release of therapeutic agents from carboxylic acid ortho ester polymers and to a process for the preparation of said pharmaceutical compositions.

BACKGROUND OF THE INVENTION

Carboxylic acid ortho ester polymers consisting essentially of monomer repeating units of the partial formula

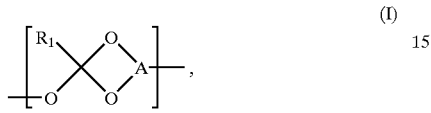
(I)

wherein $R_1$ represents hydrogen or $C_{1-4}$-alkyl and A represents a hydrocarbon chain of the formula

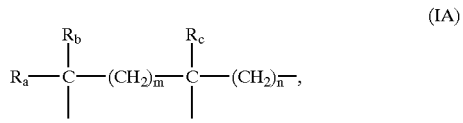
(IA)

wherein $R_a$, $R_b$ und $R_c$ independently of one another represent hydrogen or $C_{1-4}$-alkyl, and m and n independently of one another represent zero or integers from one to three; methods for preparing such ortho esters and their utility as carriers in so-called controlled release pharmaceutical compositions have been disclosed in Published International Patent Application (WO) 91/03510, International Publication Date: Aug. 23, 1990.

The slow hydrolysis of these carboxylic acid ortho ester polymers and the controlled release of therapeutic agents from the polymer matrix has been disclosed in Published International Patent Application (WO) 93/00383, International Publication Date: Jun. 18, 1992. Under physiologically acceptable conditions of pH 7.4, the hydrolysis of the ortho ester polymer (1) has been observed. This hydrolysis could formally be regarded as the reversal of the polymerisation step, whereupon a triol of the formula

(II)

is generated and the acid $R_1$—COOH is being liberated. When an carboxylic acid ortho ester polymer consisting essentially of monomer repeating units of the partial formula

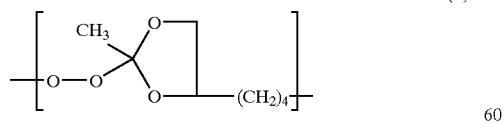
(I')

is hydrolyzed, the acid $CH_3COOH$ is liberated. Upon progressive hydrolysis of the ortho ester polymers, an increasing amount of carboxylic acids $R_1COOH$ is being liberated. This causes a decrease of the pH-level in-vitro from values of about 6.5 to 4.5 to even lower values in 1–5 days depending on the moleclur weight of the polymer.

This decreasing pH-level renders pharmaceutical compositions or administration systems containing the above-mentioned carboxylic acid ester ortho ester polymers less feasible for various types of administration, especially intramuscular, subcutaneous and intraocular administration, since it has firmly been established that the injection of a formulation with an acidic pH could trigger inflammation, cf. Sekizawa et at., *J. Toxicol. Sci.* 19, 25–35 (1994), The addition of a base to achieve neutralization is deemed unsuitable, since basic substances produce a local pH level above 8 at the site of addition. This is not acceptable for implants and for various modes of administration, especially intravenous and intraocular administration.

OBJECTS OF THE INVENTION

Accordingly, the problem to which the present invention relates may be defined as follows: It is desirable to provide a pharmaceutical dosage form for the controlled release of active agents from carboxylic acid ortho ester polymers. To solve this problem, it is necessary to maintain the pH-level in a physiologically acceptable constant range between 5.0 and 7.5.

This problem has been solved by adding a pharmaceutically acceptable salt of an acid, which together with the acid being liberated from the decomposition of the carboxylic acid ortho ester polymer (I) forms a buffer system in a physiologically acceptable pH-range.

GENERAL DESCRIPTION OF THE INVENTION

The present invention, therefore, relates to a pharmaceutical composition for the controlled release of therapeutic agents from a polymer comprising:

a) the therapeutic agent or a combination of therapeutic agents to be administered;

b) a bioerodible carboxylic acid ortho ester polymer consisting essentially of monomer repeating units of the partial formula

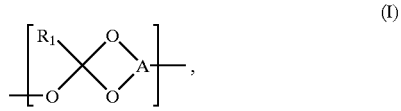
(I)

wherein $R_1$ represents hydrogen or $C_{1-4}$-alkyl, and A represents a hydrocarbon chain of the formula

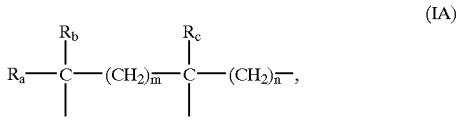
(IA)

wherein $R_a$, $R_b$ und $R_c$ independently of one another represent hydrogen or $C_{1-4}$-alkyl, and m and n independently of one another represent zero or integers from one to three;

c) a pharmaceutically acceptable salt of an acid, which together with the acid $R_1$—COOH being liberated from the decomposition of the carboxylic acid ortho ester polymer (I) forms a buffer system in a physiologically acceptable pH-range; and the following optional components:

d) further pharmaceutically acceptable additives; and/or e) a pharmaceutically acceptable carrier liquid.

The pharmaceutical composition is suitable for implants and also for various types of administration, especially parenteral administration by injection, e.g. intramuscular, subcutaneous, subconjunctival, intraocular or periodental administration. The controlled release of the active agent administered follows an approximate "zero order" pattern (constant amounts of active agent are released within defined time periods). The decomposition products of the polyortho esters defined above are physiologically acceptable and no removal of undesirable decomposition products from the site of administration is deemed necessary.

The general terms used throughout the specification of this invention are preferably defined as follows:

The term pharmaceutical composition defines a mixture containing the therapeutic agent or combination of therapeutic agents to be administered in the selected dosage form to a host in a therapeutic method of treating the disease or condition indicated. Intramuscular and intraocular administration of the pharmaceutical composition are particularly preferred.

Component a)

The term therapeutic agent as used herein is intended to define a compound or composition of matter which, when administered to a human being or an animal, induces a desired pharmacological and/or physiological effect by local and/or systemic action. In general, this term includes therapeutic or prophylactic agents in all major therapeutic/ prophylactic areas of medicine. Suitable therapeutic agents include the following pharmaceutical agents: antiinflammatory agents, for example dexamethasone, sodium dexamethasone sulfate, hydrocortisone or prednisolone, coronary dilators, for example nifedipine, isosorbitol dinitrate, nitroglycerine, diltiazem, trapidil, dipyridamole or dilazep, prostaglandins, for example prostaglandin $E_1$, $E_2$ or $F_{2A}$, peripheral vasodilators, for example ifenprodil, cinepazet maleate, cyclandelate, cinnarizine or pentoxyphylline, antibiotics, for example ampicillin, amoxycillin, cephalexin, cephradine, cefroxadin, cefaclor, erythromycin, bacampicillin, minocycline or chloramphenicol, antispasmodics, for example propantheline, atropine or scopolamine, antitussives and antiasthmatics, for example theophylline, aminophylline, methylephedrine, procatechol, trimethoquinol, codeine, clofedanolol or dextromethorphan, diuretics, for example furosemide or acetazolamide, muscle relaxants, for example chlorphenesin carbamate, tolperison, eperison or baclofen, mild tranquilisers, for example oxazolam, diazepam, clotiazepam, medazepam, temazepam or fludiazepam, potent tranquilisers, for example sulpiride, clocapramine or zotepin, beta-blockers, for example pindolol, propranolol, carteolol, oxprenolol, metoprolol or labetalol, antiarrhythmics, for example procainamide, disopyramide, ajimalin or quinidine, antigout agents, such as allopurinol, anticoagulants, such as ticlopidine, antiepileptics, for example phenytoin or valproat, antihistamines, for example chlorpheniramine, clemastine, mequitazine, alimemazine, cyproheptadine, agents for treating nausea and dizziness, for example diphenidol, methochlopromide, domperidone or betahistine, antihypertensives, for example reserpine, rescinnamine, methyldopa, prazosin, clonidine or budralazin, sympathomimetics, for example dihydroergotamine, isoproterenol or etilefrin, expectorants, for example bromhexine, carbocisteine, L-ethylcysteine or L-methylcysteine, oral antidiabetics, for example glibenclamide or tolbutamide, cardiovascular agents, for example ubidecarenon or adenosine.

Therapeutic agents can be converted into pharmaceutically acceptable salts, for example into a hydrobromide, hydrochloride, mesylate, acetate, succinate, lactate, tartrate, fumarate, sulfate or maleate salt.

Preferred therapeutic agents are immunosuppressants, such as cyclosporin, cytostatics, such as edatrexate (10-EDAM), doxorubicin, cytarabine, trifosamide, cyclophosphamide, fluorouracil or methotrexate and zinc phthalocyanine as well as water-soluble sulfo derivatives of phthalocyanine, for example tetrasulfophthalocyanine, which can be used in photo-dynamic chemotherapy.

The therapeutic agents mentioned above are present in the pharmaceutical composition either as individual agents or in fixed combinations with other therapeutic agents. The dose administered is the dose prescribed for each agent, the mode of administration intended and the disease and condition indicated for therapy.

In preferred embodiments of the invention, therapeutic agents are administered by subconjunctival and intraocular injection, such as 5-fluorouracil (5-FU) and mitomycin, after glaucoma filtering surgery; 5-FU or dexamethasone for the treatment of proliferative vitroretinopathy; by subcutaneous and intramuscular injection, such as naltrexone as narcotic antagonisms; insulin for treatment of diabetes mellitus, norethisterone and levonorgestrel as contraceptive agents; demineralized bone matrix and bone graft agents for bone formation; 5-FU and naltrexone for the treatment of tumors, pyrimethamine or halofantrine for prophylaxis of malaria, homosulphanilamid for the treatment of burned skin, or tetracycline for periodontal injection.

Component b)

A suitable bioerodible carboxylic acid ortho ester polymer present in the pharmaceutical composition consists essentially of monomer repeating units of the partial formula

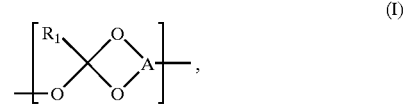

wherein $R_1$ represents hydrogen or $C_{1-4}$-alkyl and A represents a hydrocarbon chain of the formula

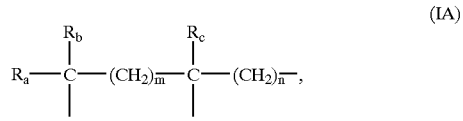

wherein $R_a$, $R_b$ und $R_c$ independently of one another represent hydrogen or $C_{1-4}$-alkyl, and m and n independently of one another represent zero or integers from one to three;

A particularly preferred carboxylic acid ortho ester polymer present in the pharmaceutical composition consists essentially of monomer repeating units of the partial formula

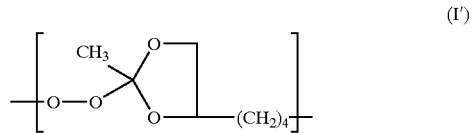

The term bioerodible as used herein to describe the properties of the defined ortho ester polymers is synonymous with the term biodegradable. These terms denote the property of a body of solid or semisolid polymers to undergo degradation, erosion and solubilization as a result of hydrolysis of labile linkages at the physiological conditions of use.

Monomer repeating units of the partial formula I are structurally recurring units or monomer units of the carboxylic acid ortho ester polymers provided by the present invention. The monomer repeating units may be the same or different; when different, they may be arranged in block sequential order or random fashion. When all monomer repeating units are the same or identical, the polymer is called a homopolymer. When there are 2 or more different monomer repeating units in a polymer, the polymer is called a copolymer. The present invention comprises pharmaceutical compositions containing copolymers and homopolymers. Homopolymers are particularly preferred.

In the monomer repeating units of the partial formula (I) $R_1$ represents hydrogen or $C_{1-4}$-alkyl, e.g. methyl, ethyl, n- or isopropyl or n-butyl. Methyl is particularly preferred. In ortho ester polymers wherein $R_1$ represents methyl, acetic acid is liberated upon hydrolysis of the polymer. in a hydrocarbon chain of the formula

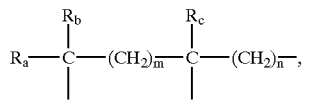
(IA)

$R_a$, $R_b$ and $R_c$ preferably represent hydrogen. One or two of $R_a$, $R_b$ and $R_c$ may represent hydrogen and the other(s) $C_{1-4}$-alkyl, particularly methyl. In the alternative, $R_a$, $R_b$ and $R_c$ may all represent identical or different $C_{1-4}$-alkyl groups. The parameters m and n independently of one another represent zero or integers from one to three; m preferably is zero and n preferably is three.

The preparation of the carboxylic acid ortho ester polymers is known and comprises the following steps: A triol of the formula

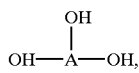
(II)

wherein A represents the alkylene chain of the formula IA defined above, is reacted under the conditions of a condensation reaction with a carboxylic acid ortho ester of the formula

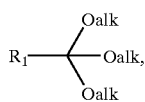
(III)

wherein Oalk represents the $C_{1-4}$-alkoxy group and $R_1$ is as defined above, to give an ortho ester polymer consisting essentially of monomer repeating units of the partial formula

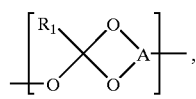
(I)

wherein A represents the alkylene chain of the formula IA.

The synthesis reaction of the ortho ester monomer (III) and the triol (II) is carried out neat or in an aprotic solvent such as tetrahydrofuran (THF), cyclohexane, ethylene glycol dimethyl ether (glyme) or the like. Typical concentrations of the reactants may range from essentially 100% (neat) down through about 10% by weight or lower, when solvent is used. The presence of anhydrous conditions is maintained. The reaction can be carried out under reflux conditions and thus, depending upon the solvent, at temperatures in the range of 50–150° C., preferably 50–90° C. The approximate molar ratio of the reactants is about 1:1. It is typically preferred to carry out the reaction in the presence of an acid catalyst. Examples of suitable acid catalysts include p-toluenesulfonic acid and methanesulfonic acid. The amount of acid catalyst can range from 0% (based on its optional presence) to about 1% molar (based on the amount of triol present).

A preferred synthesis comprises reacting under the conditions of a condensation reaction mentioned above the trial of the formula

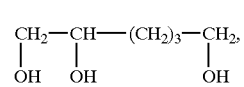
(II')

with the acetic acid ester of the formula

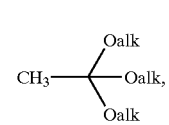
(III')

wherein Oalk represents the $C_{1-4}$-alkoxy group, to give an acetic acid ortho ester polymer consisting essentially of monomer repeating units of the partial formula

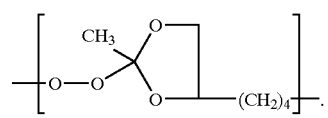
(I')

Component c)

A pharmaceutically acceptable salt of an acid, which together with the acid $R_1$—COOH being liberated from the decomposition of the ortho ester polymer (I) forms a buffer system in a physiologically acceptable pH-range, is defined by the definition of $R_1$ in the ortho ester polymer (I). The pH-level in a physiologically acceptable range is between 6.5 and 7.5. The pH of 7.5 must not be exceeded when intraocular or intramuscular administration is intended.

When $R_1$ is hydrogen, formic acid will be liberated upon hydrolysis of the ortho ester polymer (I). A suitable pharmaceutically acceptable salt of formic acid is, e.g. sodium or potassium formiate. When $R_1$ is methyl, acetic acid will be liberated upon hydrolysis. A pharmaceutically acceptable salt of acetic acid is, e.g. sodium or potassium acetate.

When $R_1$ is ethyl, n-propyl or n-butyl, the corresponding $C_3$-, $C_4$-, or $C_5$-carboxylic acids will be liberated upon hydrolysis. Preferred pharmaceutically acceptable acids of these acids are the sodium salts. The addition of pharmaceutically acceptable salts of other acids is also possible. Their structure is unrelated with the group $R_1$ in the ortho ester polymer (I), but these salts also form together with the acid $R_1$—COOH being liberated from the decomposition of the ortho ester polymer (I) a buffer system in the physiologically acceptable pH-range defined above. Such salts are, for example, sodium citrate, salts from amino acids, sodium ascorbate, glycolate, lactate, tartrate, maleate, fumarate, maleinate, succinate, benzoate and others.

Pharmaceutically acceptable salts of the acids defined above have the particular advantage of buffering the pharmaceutical composition on acceptable pH-levels. In the beginning and in all subsequent stages of the hydrolytic decomposition of the ortho ester polymer (I) biocompatibility is maintained. Initial raises of the pH-level when decomposition begins, to basic pH-levels and subsequent lowering to acidic pH-levels is avoided.

The amount of the salt added is determined by the amount of the ortho ester polymer present in the pharmaceutical composition. The addition of molar equivalent amounts of salt is preferred. For each molar amount of acid liberated, the addition of a molar amount of the above-defined salt is suggested. The salt may also be added in less than equivalent and excess amounts, e.g. up to 2 molar equivalents.

Component d)

Suitable pharmaceutically acceptable additives are determined by the dosage form for the intended mode of administration, e.g. parenteral administration. A preferred mode of administration is especially intramuscular and subcutaneous, but also topical, e.g. ocular.

Additives for topical formulations are listed in standard textbooks, e.g. *Remington's Pharmaceutical Sciences* or *Hagers Handbuch der Pharmazeutischen Praxis*. Topical formulations are in particular creams, ointments, gels, pastes or topically administered aerosols and also suspensions of nanoparticles or ophthalmic compositions. Suitable additives for topical and especially ophthalmic compositions are in particular inert carriers, solubilizers, tonicity-increasing agents, buffer substances, preservatives, thickeners, and other adjuncts. Such additives are e.g. vegetable oil, mineral oil containing hydroxyethyl cellulose, ethyl oleate, carboxymethyl cellulose, polyvinylpyrrolidone, and other non-toxic water-soluble polymers intended for ophthalmic use, e.g. cellulose ethers such as methyl cellulose, alkali metal salts of carboxymethyl cellulose or hydroxymethyl, hydroxyethyl, or hydroxypropyl cellulose, acrylates or methacrylates such as salts of polyacrylic acid or ethyl acrylate, polyacrylamides, natural products such as gelatin, alginates, pectins, tragacanth, karaya gum, xanthan gum, carrageenan, agar or acacia, starch derivatives such as starch acetate and hydroxypropyl starch, and also other synthetic additives such as polyvinyl alcohol, polyvinylpyrrolidone, polyvinyl methyl ether, polyethylene oxide, preferably crosslinked polyacrylic acid, such as neutral Carbopol® or mixtures of these polymers.

Tonicity-enhancing agents are, for example, ionic compounds, such as alkali metal or alkaline earth metal halides, e.g. $CaCl_2$, KBr, KCl, LiCl, NaI, NaBr, or NaCl, or boric acid. Non-ionic tonicity-enhancing agents are, for example, urea, glycerol, sorbitol, mannitol, propylene glycol, or dextrose. Sufficient tonicity-enhancing agent is added that the ophthalmic composition has an osmolality in a preferred range of about 50 to 400 mOsmol.

Examples of preservatives are quaternary ammonium salts such as cetrimide, benzalkonium chloride, alkylmercury salts of thiosalicylic acid such as thiomersal, phenylmercury nitrate, acetate, or borate, parabens such as methylparaben or propylparaben, alcohol, e.g. chlorobutanol, benzyl alcohol, or phenylethanol, guanidine derivatives, e.g. chlorhexidine, or polyhexamethylenebiguanide, or sorbic acid. If desired, the amount of preservative which is necessary to ensure sterility is added to the ophthalmic composition.

Component e)

A suitable pharmaceutically acceptable carrier liquid is defined by the intended mode of administration. If intramuscular administration is intended, oily carrier liquids, such as propylene glycol, polyethylene glycol, sesame oil or olive oil, but also lecithin, may be added. Carrier liquids are particularly preferred when intramuscular, or intraocular administration is intended. The carrier liquid ethanol, if desired, is added in the degree of purity (96%) prescribed for injection formulations in accordance with the regulations of national pharmacopoeias, such as The U.S. Pharmacopoeia (USP) or Deutsches Arzneibuch (DAB). The proportion of ethanol can vary within wide limits from approximately 1% to approximately 50%, preferably from approximately 1% to approximately 10%. The carrier liquid water has the degree of purity prescribed for intravenous administration and is germ- and pyrogen-free in accordance with the regulations of the national pharmacopoeias.

PREFERRED EMBODIMENTS OF THE INVENTION

The present invention particularly relates to a pharmaceutical composition comprising:

a) the therapeutic agent or a combination of therapeutic agents to be administered;

b) a bioerodible carboxylic acid ortho ester polymer consisting essentially of monomer repeating units of the partial formula

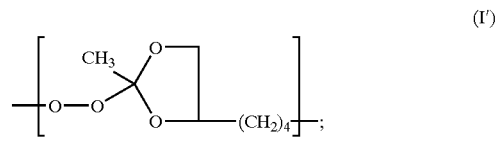

c) a pharmaceutically acceptable salt of an acid, which together with the acid $CH_3COOH$ being liberated from the decomposition of the ortho ester polymer (I') forms a buffer system in a physiologically acceptable pH-range; and, optionally, d) further pharmaceutically acceptable additives.

An especially preferred embodiment of the invention relates to a pharmaceutical composition comprising:

a) the therapeutic agent or a combination of therapeutic agents to be administered;

b) a bioerodible carboxylic ortho ester polymer consisting essentially of monomer repeating units of the partial formula (I');

c) the alkali metal salt $X^+CH_3COO^-$, which together with the acid $CH_3COOH$ being liberated from the decomposition of the ortho ester polymer (I') forms a buffer system in the physiologically acceptable pH-range of 5.5–7.5; and, optionally, d) further pharmaceutically acceptable additives.

A highly preferred embodiment of the invention relates to a pharmaceutical composition comprising:

a) the therapeutic agent or a combination of therapeutic agents to be administered;

b) a non-rigid, bioerodible ortho ester polymer consisting essentially of monomer repeating units of the partial formula (I');

c) the sodium salt $Na^+CH_3COO^-$, which together with the acid $CH_3COOH$ being liberated from the decomposition of the ortho ester polymer (I'), forms a buffer system;

d) further pharmaceutically acceptable additives suitable for intraocular administration.

The present invention also relates to a process for the preparation of the above-mentioned pharmaceutical composition which process comprises preparing a non-rigid, bioerodible ortho ester polymer consisting essentially of monomer repeating units of the partial formula (I) mentioned above; and adding and mixing, in any order of the subsequent process steps, component a), the therapeutic agent or a combination of therapeutic agents to be administered; component c), a pharmaceutically acceptable salt of an acid, which together with the acid $R_1$—COOH being liberated from the decomposition of the ortho ester polymer (I), forms a buffer system in a physiologically acceptable pH-range; and, optionally, component d), further pharmaceutically acceptable additives; and/or component e), a pharmaceutically acceptable carrier liquid.

Mixing can be effected by vigorous shaking when using a dispersing machine, for example a Vortex mixer, or using dispersing machines produced by IKA (Staufen, Germany), a static mixer and conventional stirring machines having a propeller or paddle blade or using a magnetic stirrer or phase mixer. In order to obtain an especially homogeneous mixture, stirring is carried out at high speed. Approximately from 0.1 to 50% by weight of the constituents (without the water component), based on the total weight of the mixture, preferably approximately from 2 to 20% by weight, can be dispersed in the carrier liquid.

The following Example illustrates the invention:

EXAMPLE 1 a) Synthesis of The Ortho Ester Polymer 34.68 g (300 mMol) of trimethyl ortho acetate (99%—Aldrich Chemie, Steinheim Germany) are mixed under anhydrous conditions with 40.25 g (300 mMol) of 1,2,6-hexanetriol (98%—Aldrich). The mixture is introduced into a round bottom flask, placed on a magnetic stirrer with 400 ml of cyclohexane added. The reaction is catalyzed by the addition of 25 mg p-TSA: p-toluenesulfonic acid (Fluka). The reaction flask is equipped with a distillation column and heated to 120° C. under argon atmosphere and vigorous stirring. In a first step, the reaction by-product methanol is removed at 54° C. during the first 4 h of the distillation. In a second step, the temperature at the column head climbs above 54° C. The distillation flow is decreased and the solution is heated for an additional 6 h until the boiling point of 81° C. is reached. The solution then is cooled to room temperature, and 10 drops of triethylamine (Fluka) are added to neutralize the acid catalyst. Excess solvent is pured off and the polymer is dried overnight under vacuum at 40° C. The polymer is then purified by dissolution in 100 ml of tetrahydrofurane (THF) and and precipitation in 500 ml anhydrous methanol containing 10 drops of triethylamine. After separating off the solvent, the polymer is dried under high vacuum for 48 h. An 0.2μ air filter is added during the solvent evaporation in order to avoid air contamination when the vacuum is broken. No bacterial growth has been observed after 48 h of incubation of test samples at 37° C.

b) Preparation of the Drug Loaded Polymer

A 5-fluorouracil (5-FU) loaded polymer is prepared by mixing under laminar flow 25 mg of gamma-sterilized (2.0 Mrad) 5-FU and 12.5 mg of sodium acetate and dispersing the mixture with 2.5 g of aseptically prepared poly ortho ester polymer. This mixture is suitable as implant or for intraocular administration.

c) pH Determination

The pH was measured during hydrolysis of the ortho ester polymer in order to assess the decrease of pH induced by the release of acetic acid.

1 g (w/w) ortho ester polymer (POE) and 10 ml 0.9% sodium chloride solution were placed in an incubator (Haling, Aigle, Switzerland) at 37° C. under light shaking (100 U/min). The pH measurements were taken every days during the first week and then every week until degradation was complete, with a pH-meter Mettler DL25 (N änikon-Uster, Switzerland) and a combined pH-glass microelectrode.

Some results are shown in the accompanying drawing in which

BRIEF DESCRIPTION OF THE DRAWINGS

As shown in FIG. 1 stabilization of the pH level between 5 and 6 is observed upon addition of sodium acetate. Without addition of acetate the pH level falls below 4 after one week. and thereafter further to 2.5.

FIG. 2 shows that the release of 5-FU is only slightly affected by the adjunction of 0.5% sodium acetate.

Figure 1:
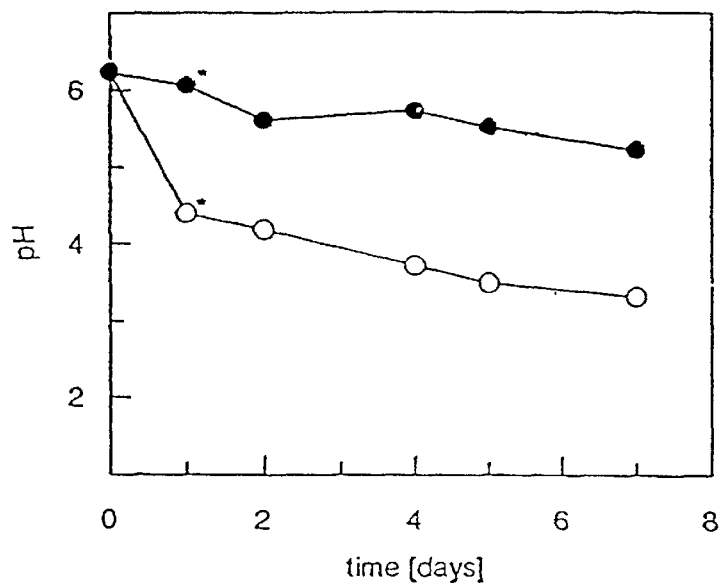
FIG. 1 is a graph showing pH profiles of the POE containing 5-FU, with or without addition of sodium acetate.
Figure 2:
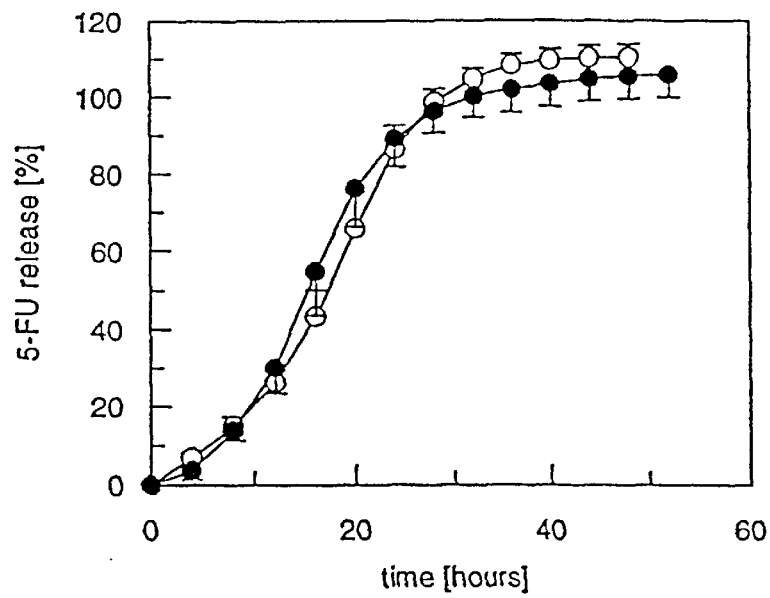
FIG. 2 is a graph showing 5-FU release profiles with and without addition of acetate.

What is claimed is:

1. A pharmaceutical composition for the controlled release of therapeutic agents from a polymer matrix comprising:

a) the therapeutic agent or a combination of therapeutic agents to be administered;

b) a bioerodible carboxylic acid ortho ester polymer consisting essentially of monomer repeating units of the partial formula:

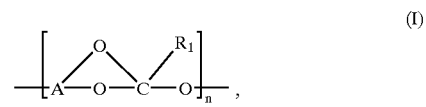

wherein R1 represents hydrogen or C1–4-alkyl and A represents a hydrocarbon chain of the formula

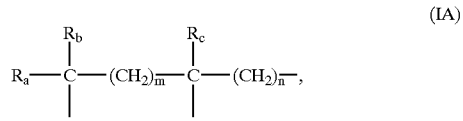

wherein Ra, Rb, and Rc independently represent hydrogen or C1–4-alkyl, and m and n independently represent zero or integers from one to three;

c) a pharmaceutically acceptable salt of an acid, which together with the acid R1-COOH being liberated from the decomposition of the ortho ester polymer (I) forms a buffer system in a physiologically acceptable pH range; and the following optional components;

d) further pharmaceutically acceptable additives; and or e) a pharmaceutically acceptable carrier liquid.

2. A pharmaceutical composition according to claim 1 comprising:

a) the therapeutic agent or a combination of therapeutic agents to be administered;

b) a bioerodible carboxylic acid ortho ester polymer consisting essentially of monomer repeating units of the partial formula

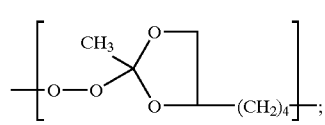 (I')

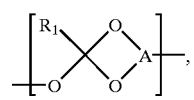 (I)

wherein A represents the alkylene chain of the formula IA defined in claim 1; and adding, in any order of the subsequent process steps, component a), the therapeutic agent or a combination of therapeutic agents to be administered; component c), a pharmaceutically acceptable salt of an acid, which together with the acid $R_1$—COOH being liberated from the decomposition of the ortho ester polymer (I), forms a buffer system in a physiologically acceptable pH-range; and, optionally, component d), further pharmaceutically acceptable additives; and/or component e), a pharmaceutically acceptable carrier liquid.

c) a pharmaceutically acceptable salt of an acid, which together with the acid $CH_3COOH$ being liberated from the decomposition of the ortho ester polymer (I') forms a buffer system in a physiologically acceptable pH-range; and, optionally, d) further pharmaceutically acceptable additives.

3. A pharmaceutical composition according to claim 2 comprising:

a) the therapeutic agent or a combination of therapeutic agents to be administered;

b) a bioerodible carboxylic ortho ester polymer consisting essentially of monomer repeating units of the partial formula (I');

c) the alkali metal salt $X^+CH_3COO^-$, which together with the acid $CH_3COOH$ being liberated from the decomposition of the ortho ester polymer (I') forms a buffer system in the physiologically acceptable pH-range of 5.5–7.5; and, optionally, d) further pharmaceutically acceptable additives.

4. A pharmaceutical composition according to claim 3 comprising:

a) the therapeutic agent or a combination of therapeutic agents to be administered;

b) a non-rigid, bioerodible ortho ester polymer consisting essentially of monomer repeating units of the partial formula (I');

c) the sodium salt $Na^+CH_3COO^-$, which together with the acid $CH_3COOH$ being liberated from the decomposition of the ortho ester polymer (I'), forms a buffer system;

d) further pharmaceutically acceptable additives suitable for intraocular administration.

5. A process for the preparation of the pharmaceutical composition according to claim 1, which comprises reacting under the conditions of a condensation reaction a triol of the formula

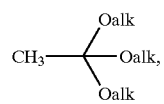 (II)

wherein A represents the alkylene chain of the formula IA defined in claim 1, with a carboxylic acid ortho ester of the formula

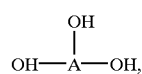 (III)

wherein Oalk represents the $C_{1-4}$-alkoxy group, to give a carboxylic acid ortho ester polymer consisting essentially of monomer repeating units of the partial formula 6. A process for the preparation of the pharmaceutical composition according to claim 5, which comprises reacting under the conditions of a condensation reaction the triol of the formula

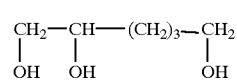 (II')

with the acetic acid ester of the formula

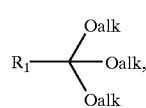 (III')

wherein Oalk represents the $C_{1-4}$-alkoxy group, to give an ortho ester polymer consisting essentially of monomer repeating units of the partial formula

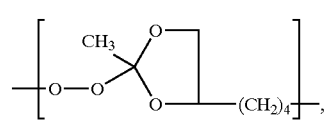 (I')

and adding, in any order of the subsequent process steps, component a), the therapeutic agent or a combination of therapeutic agents to be administered; component c), a pharmaceutically acceptable salt of an acid, which together with the acid $CH_3COOH$ being liberated from the decomposition of the ortho ester polymer (I'), forms a buffer system in a physiologically acceptable pH-range; and, optionally, component d), further pharmaceutically acceptable additives; and/or component e), a pharmaceutically acceptable carrier liquid.

7. A process according to claim 6, which comprises adding component c), the alkali metal salt $X^+CH_3COO^-$, which together with the acid $CH_3COOH$ being liberated from the decomposition of the ortho ester polymer (I') forms a buffer system in the physiologically acceptable pH-range of 5.5–7.5.

8. A process according to claim 7, which comprises adding component c), the sodium salt $Na^+CH_3COO^-$, which together with the acid $CH_3COOH$ being liberated from the decomposition of the ortho ester polymer (I') forms a buffer system.

* * * * *

UNITED STATES PATENT AND TRADEMARK OFFICE
CERTIFICATE OF CORRECTION

PATENT NO. : 6,440,460 B1  
DATED : August 27, 2002  
INVENTOR(S) : Gurny et al.

It is certified that error appears in the above-identified patent and that said Letters Patent is hereby corrected as shown below:

Column 1,
Line 55, delete the formula and insert in place thereof corrected formula

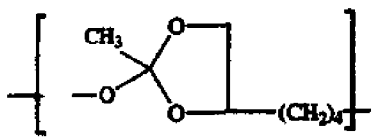

Column 4,
Line 55, delete the formula and insert in place thereof corrected formula

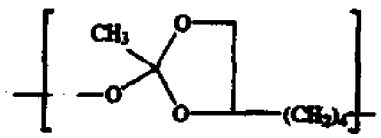

Column 6,
Line 35, delete the formula and insert in place thereof corrected formula

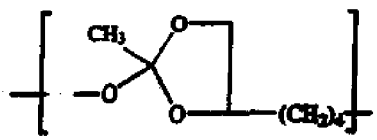

Column 8,
Line 39, delete the formula and insert in place thereof corrected formula

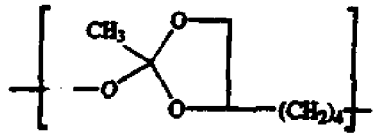

UNITED STATES PATENT AND TRADEMARK OFFICE
CERTIFICATE OF CORRECTION

PATENT NO. : 6,440,460 B1
DATED : August 27, 2002
INVENTOR(S) : Gurny et al.

It is certified that error appears in the above-identified patent and that said Letters Patent is hereby corrected as shown below:

Column 11,
Line 5, delete the formula and insert in place thereof corrected formula

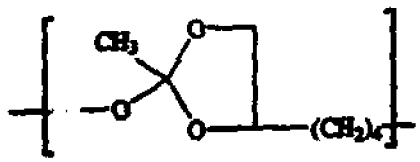

Column 12,
Line 40, delete the formula and insert in place thereof corrected formula

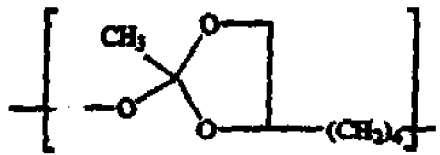

Signed and Sealed this

Fifth Day of April, 2005

JON W. DUDAS
*Director of the United States Patent and Trademark Office*